United States Patent
Fristedt et al.

(10) Patent No.: US 6,892,807 B2
(45) Date of Patent: May 17, 2005

(54) SEAT WITH TEMPERATURE CONTROL AND VENTILATION AND SAFETY SYSTEM FOR A VEHICLE

(75) Inventors: Tommy Fristedt, Bottnaryd (SE); Daniel Josefsson, Falköping (SE)

(73) Assignee: Kongsberg Automotive AB (SE)

( * ) Notice: Subject to any disclaimer, the term of this patent is extended or adjusted under 35 U.S.C. 154(b) by 189 days.

(21) Appl. No.: 10/333,380

(22) PCT Filed: Jul. 2, 2001

(86) PCT No.: PCT/SE01/01521

§ 371 (c)(1), (2), (4) Date: Jan. 17, 2003

(87) PCT Pub. No.: WO02/06914

PCT Pub. Date: Jan. 24, 2002

(65) Prior Publication Data

US 2004/0118555 A1 Jun. 24, 2004

(30) Foreign Application Priority Data

Jul. 19, 2000 (SE) ................................ 0002690

(51) Int. Cl.⁷ ................................ B60H 1/00
(52) U.S. Cl. .................. 165/202; 165/222; 165/237; 165/267; 165/288; 62/244; 237/12.3 A; 219/202
(58) Field of Search .................... 165/41, 42, 43, 165/202, 203, 204, 222, 237, 253, 254, 267, 268, 287, 288, 290; 62/180, 244; 237/12.3 R, 12.3 A; 219/202

(56) References Cited

U.S. PATENT DOCUMENTS

| | | | | |
|---|---|---|---|---|
| 4,572,430 A | * | 2/1986 | Takagi et al. | 237/12.3 R |
| 5,921,314 A | | 7/1999 | Schuller et al. | |
| 5,934,748 A | | 8/1999 | Faust et al. | |
| 6,068,332 A | * | 5/2000 | Faust et al. | 297/180.13 |
| 6,079,485 A | * | 6/2000 | Esaki et al. | 219/202 |
| 6,105,667 A | * | 8/2000 | Yoshinori et al. | 219/202 |
| 6,263,530 B1 | * | 7/2001 | Feher | 165/185 |
| 6,552,442 B2 | * | 4/2003 | Liao et al. | 165/43 |

FOREIGN PATENT DOCUMENTS

| | | |
|---|---|---|
| EP | 0 227 610 A1 | 7/1987 |
| EP | 0 929 055 A1 | 7/1999 |

* cited by examiner

Primary Examiner—Ljiljana Ciric
(74) Attorney, Agent, or Firm—Lerner, David, Littenberg, Krumholz & Mentlik, LLP

(57) ABSTRACT

Methods and apparatus for controlling the temperature of a seat such as a vehicle seat are disclosed. The apparatus includes an electrical heater disposed in the seat, a cooling unit such as a cooling element and a fan, a detector for detecting the temperature associated with the electrical heater, and a controller for controlling the electrical heater and the cooler based upon the detected temperature and upon the humidity algorithm comprising a predetermined set of calculations of the humidity of air at different temperatures.

20 Claims, 8 Drawing Sheets

SEAT WITH TEMPERATURE CONTROL AND VENTILATION AND SAFETY SYSTEM FOR A VEHICLE

FIELD OF THE INVENTION

The present invention relates to a method and apparatus for cooling a seat. More particularly, the present invention relates to the cooling and/or ventilation of electrically heatable seats for travellers in a vehicle.

BACKGROUND OF THE INVENTION

For reasons of both comfort and security, ventilation and/or cooling of seats, for example in vehicles, is used. The driver's seat, as well as the other seats in the vehicle, may thus be arranged to be cooled by means of special cooling devices, for example in the form of electrical Peltier elements, or by means of a fan that blows on the current surface, or by a combination of these devices. Such a cooling element or fan may be placed in the seat or in the backrest of a seat when it is manufactured. Further, the cooling element or the fan may be connected to a current supply unit that supplies current. The control systems according to previously known technology are of the time control type, i.e. they have pure timer functions, which during certain predetermined time periods control the cooling element to a suitable temperature and the fan to a suitable number of revolutions.

A problem with previously known cooling devices relates to the desire that the seat have an accurately adjusted temperature and dryness on its surface, i.e. on the surface that the traveller in the vehicle senses. For this purpose, the temperature of the cooling element and/or the intensity of the fan may be controlled by means of a sensor unit, e.g. a temperature sensor that is arranged in the seat and that is connected to a control unit. By means of the detector unit and the control unit, the available temperature may be detected. The control unit also comprises current feeding circuits, which e.g. may be based on transistor or relay technology, for feeding current to the cooling element and/or the fan.

Although these previously known systems normally provide reliable cooling and dryness on the surface of a vehicle seat, they are, however, afflicted with certain disadvantages. Such disadvantages relate to the fact that previously known systems, whether timer controlled or manually controlled, and with a cooling element and a fan, provide for a rather uncontrolled cooling and drying of the seat, due to the fact that the cooling by means of the cool airflow almost exclusively takes place by convection, which may lead to local over-cooling of the user which in itself is a health hazard.

A further disadvantage with previously known systems is that a warm and damp user receives cold air directly on the body, which during the drying of the seat and the user may be sensed as cold and damp, and thus unpleasant, by the user. Even if the cooling does not take place by means of blowing of the air directly on the body, but bye means of conductive cooling of the seat, a cold and damp surface may be sensed as unpleasant.

A further disadvantage with previously known systems is that the quick cooling of the seat affects the material of the seat negatively in such a way that the material of the seat becomes less comfortable at low temperatures.

Further disadvantages with previous systems is that a control device with special sensors for a cooling device for a seat occupies significant space and is expensive.

One object of the present invention is thus to provide enhanced cooling, drying, temperature control and ventilation of a vehicle seat comprising a cooling device, where the disadvantages stated above are eliminated and which provides a surface temperature and surface dryness which, during adjustment, becomes more comfortable for the traveller.

SUMMARY OF THE INVENTION

In accordance with the present invention, these and other objects have now been realized by the discovery of apparatus for controlling the temperature of a seat including a lower surface and an upper sitting surface comprising an electrical heater disposed in the seat, cooling means comprising a cooling element and a fan operatively associated with the seat, a detector for detecting the temperature associated with the electrical heater, and a controller for controlling the electrical heater and the cooling means based upon the detected temperature and upon a humidity algorithm comprising a predetermined set of calculations of the humidity of air at a plurality of different temperatures. Preferably, the detector detects the temperature based at least in part upon conductive cooling from the cooling means, convective cooling from the cooling means, and conductive heating from the electrical heater.

In accordance with one embodiment of the apparatus of the present invention, the cooling means is disposed in the seat.

In accordance with another embodiment of the apparatus of the present invention, the apparatus includes an air conditioning unit, and the cooling means is operatively associated with the air conditioning unit. Preferably, the fan is operatively associated with the air conditioning unit.

In accordance with yet another embodiment of the apparatus of the present invention, the cooling means comprises an air conditioning unit operatively disposed with respect to the seat. In a preferred embodiment, the fan is operatively associated with the air conditioning unit.

In accordance with another embodiment of the apparatus of the present invention, the fan is disposed to blow air towards the lower surface of the seat and towards the upper sitting surface.

In accordance with another embodiment of the apparatus of the present invention, the fan is disposed to draw air from the upper sitting surface towards the lower surface of the seat.

In accordance with another embodiment of the apparatus of the present invention, the apparatus includes a humidity sensor operatively disposed with respect to the seat for detecting humidity of the upper sitting surface of the seat.

In accordance with another embodiment of the apparatus of the present invention, the detector comprises a first temperature sensor operatively disposed with respect to the electrical heater and at least one second temperature sensor operatively disposed a predetermined distance from the electrical heater. Preferably, the first temperature sensor and the at least one second temperature sensor are connected to each other whereby a superposed detectable temperature value is obtained for the controller. In another embodiment, the apparatus includes a central connection between the first temperature sensor and the at least one second temperature sensor for providing information with regard to the first temperature sensor and the at least one second temperature sensor to the controller.

In accordance with another embodiment of the apparatus of the present invention, the apparatus includes an auxiliary detector for detecting a standard condition such as the driver's predetermined standard condition or the vehicle's predetermined standard condition, whereby the auxiliary detector can actuate the cooling means.

In accordance with the present invention, these and other objects have also been realized by the discovery of a method for controlling the temperature of a seat having a lower surface and an upper sitting surface comprising an electrical heater, cooling means, and a detector operatively disposed for detecting a temperature of the electrical heater, and the electrical heater and the cooling means are actuated based upon the detected temperature, the method comprising detecting a first temperature, supplying a predetermined power to the electrical heater, detecting a second temperature at a predetermined time period after the detecting of the first temperature, detecting the temperature difference between the first temperature and the second temperature, determining the humidity content of air from the first and second temperatures and the predetermined power, determining a predetermined time period based upon the humidity content of the air and the first and second temperatures and the predetermined power, and controlling the electrical heater and the cooling means based upon the predetermined time period whereby the humidity content of the air is eliminated. Preferably, the method includes detecting the temperature based upon the conductive cooling from the cooling means, the convective cooling from the cooling means, and the conductive heating from the electrical heater.

In accordance with one embodiment of the method of the present invention, the method includes employing a humidity control algorithm based upon the knowledge that certain air flows in combination with certain temperature changes correspond to air substantially free of humidity, the method including controlling either the electrical heater, the fan and/or the cooling element during drying of the seat based upon the information fed to the controller.

In accordance with another embodiment of the method of the present invention, the method comprises detecting a first temperature operatively associated with the electrical heater, detecting a second temperature at a predetermined distance from the electrical heater, whereby the first and second temperatures give rise to a temperature value, and including comparing the temperature value to a desired temperature value for performing the control thereof. Preferably, the first and second temperatures are added to a superposed common temperature value in the interval between the first and second temperatures.

In accordance with another embodiment of the method of the present invention, the method includes detecting a predetermined deviation from a driver's predetermined standard condition and/or a vehicle's predetermined standard condition, and activating at least the cooling means upon detecting the deviation.

In accordance with the present invention, the seat comprises an electrical heater and a detector unit in connection with the electrical heater for detection of a temperature at electrical heater, where the cooling device and the electrical heater are activated depending at least upon the detected temperature. This purpose is also achieved with a method where the seat comprises an electrical heater and a detector unit in connection with the electrical heater where the detector unit detects a temperature at the electrical heater, where the cooling device and the electrical heater are activated at least upon the detected temperature.

A further purpose with the present invention is to provide a security system in vehicles, by means of which a driver's attention may be drawn to the fact that a hazardous situation is at hand. This purpose is achieved with a security system in which the cooling device is controlled by means of an external detector which is arranged to detect deviations from a predetermined standard of a driver or deviations from a predetermined standard of the running conditions of the vehicle. Thus, a cooling device may be activated to draw the driver's attention to the hazardous situation. It may, for example, detect whether the driver is falling asleep, in which case the cooling device may be activated for stimulating purposes.

In light of the known technology for these existing problems, the present invention is directed towards apparatus and a method for cooling or ventilation of a seat where one obtains a quick cooling and drying of a seat and a user, without the user experiencing the disadvantages existing from that known technology. By maintaining a high degree of convective cooling, a short drying time is acquired. In order to remove the disadvantages which are afflicted with known procedures, the present invention is based on the supply of a local conductive heat supply to the user's exposed areas in order to reduce the negative local chilling, that also would lead to a shorter drying time for the seat and the user. Furthermore, in order to achieve a quick, effective, and cheap adjustment that does not occupy too much space, the present invention is based on the use of available equipment as far as possible.

With a vehicle seat, all of the seat parts, such as the sitting surface and back parts are included, i.e. the present invention may, in all of its parts, be exercised freely on all the seat parts of the seat, such as the sitting surface and the back parts. The present invention may also be used only for ventilation of the seat, i.e. when cooling is lacking. Ventilation is often more important for the back part of the seat than for the sitting surface of the seat.

BRIEF DESCRIPTION OF THE DRAWINGS

The present invention will be described below in detail in connection with the following detailed description which refers to the enclosed drawings, where.

DETAILED DESCRIPTION

The embodiments which are described in connection with the following text are not to be regarded solely as examples of the present invention, but also as a detailed description of the invention. The figures and these embodiments principally show the sitting surface of a seat, but the present invention may, in all of its parts, be exercised freely on all the parts of the seat, such as the sitting surface and the back parts. The present invention may also be used only for ventilation of the seat, i.e. when cooling is lacking. Ventilation is often more important for the back part of the seat than for the sitting surface of the seat.

Figure 1:
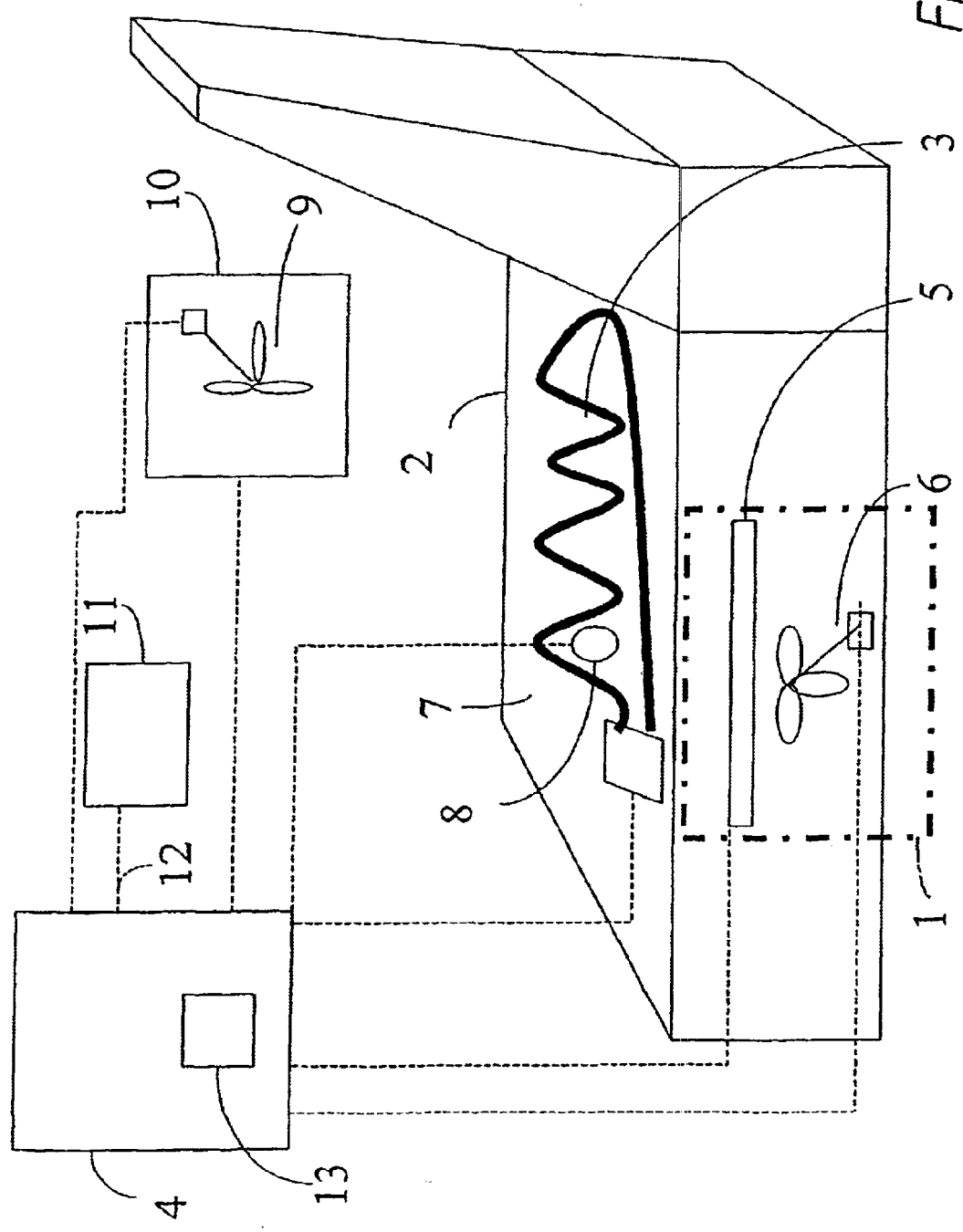
FIG. 1 is a side, elevational, schematic view of a circuit diagram showing a device according to a first embodiment of the present invention.

FIG. 1 shows a principal circuit diagram for a device according to a first embodiment of the present invention. According to the first embodiment, the invention is intended to be used in connection with a cooling device 1 (shown as a dashed square) for a seat 2 in a vehicle and an electrical heater 3 for heating the seat 2. The figure shows a control unit 4 in principle, whose internal components and connections are not shown. In the figure, electrical connections with the control unit 4 are indicated with dashed lines.

The cooling device 1 is placed in or in connection with the seat 2 and consists of a cooling element 5, e.g. a Peltier element, and a fan 6 for blowing air, here called blowing fan 6, by means of the cooling element 5 through the seat 2 in the direction towards the bottom side of the sitting surface 7, which the sitting passenger is in contact with. Both the cooling element and the blowing fan are controlled by the control unit 4 by means of electrical connections, but may also be switched to manual control. The control unit 4 controls the cooling power of the cooling element 5, for a Peltier element this is performed by control of the current intensity, and the air flow from the blowing fan 6, e.g. by changing the number of revolutions for the blowing fan 6.

According to known technology, electrically heatable seats are used in vehicles for reasons of comfort and security. The driver's seat as well as the other seats of the vehicle may thus be arranged to be heated by means of special electrical heaters in the form of electrically conductive wires placed in the form of a heating coil in respective seats. Such an electrical heater is normally placed in the seat and/or the backrest of a seat when it is manufactured. Further, the electrical heater is connected to a current supply unit that supplies current. Thus, the electrical heater may be heated to a suitable temperature.

The temperature of such a known electrical heater is controlled by means of a detector unit, e.g. comprising a temperature sensor connected to the control unit. By means of the detector unit and the control unit, the available temperature may be detected. The control unit also comprises current supply circuits (not shown), that e.g. may be based on transistor or relay technology, for supplying current to the electrical heater. Thus, the control unit is arranged to supply a current through the electrical heater until a certain desired value for the temperature in the seat is obtained, when heating is needed. The adjustment of this desired value may e.g. be performed by means of fixed resistors or by means of an adjustable potentiometer that is operated by the traveller in the vehicle, or by a control algorithm in the control unit or in an external microprocessor or computer.

According to the first embodiment of the present invention, as shown in FIG. 1, a detector unit 8 for the electrical heater 3 is used to detect the temperature in the seat 2 and to supply information about the temperature to the control unit 4, which is described in detail below. A suitable detector unit preferably consists of a thermistor, e.g. of the NTC (Negative Temperature Coefficient) type. The control unit also comprises further current supply circuits (not shown), that e.g. may be based on transistor or relay technology, for supplying current to the cooling element 5 and the fan 6. Thus, when cooling is needed, the control unit 6 is arranged to supply a specific current through the cooling element 5 and the fan 6 until a desired value for the temperature in the seat is obtained. The adjustment of this desired value may e.g. be performed by means of fixed resistors or by means of an adjustable potentiometer that is operated by the traveller in the vehicle, or by a control algorithm in the control unit 4 or in a separate control unit. The control unit 4 uses the measured values from the detector unit 8 for temperature control of the seat, both for heating and cooling of the seat, depending on how the control algorithm in the control unit is made. The control unit 4 then controls the cooling procedure for the seat 2 by determining the amount of current that is supplied to the cooling element 5, blowing fan 6 and electrical heater 3, which provides desired cooling power, air flow and heating power. If the seat 2 is very warm, e.g. when the sun has been shining on it, fast cooling of the seat is required in order to quickly provide the user with maximum comfort. When the user is also damp, e.g. after having perspired or due to the high temperature of the seat, it is also a main concern to get the user dry quickly. If only the cooling device 1 is used, the result is powerful convective cooling of the user, which leads to the user experiencing a cold and damp feeling at the contact surface between the body and the seat. In order to avoid that cold and damp feeling at the contact surface, the electrical heater 3 is used according to the present invention, which electrical heater 3 may be controlled as stated above, and is thus used to increase the temperature in the seat, which leads to a local conductive heating in the contact surface between the seat surface 7 and the user, which in turn leads to a quick drying of the user and the seat surface, at the same time as quick cooling of the whole seat takes place without the user being submitted to too fast and too large a convective cooling in the contact surface. To sum up, this arrangement provides for quick cooling of a strongly overheated seat without risk or discomfort for the user. A quick drying of the seat is also acquired, which provides for enhanced comfort. The arrangement according to the present invention also permits continuous control in order to maintain a dry seat surface 7 with a suitable temperature during a long time, e.g. during driving on longer journeys. The use of the electrical heater 3 also provides a better temperature on the seat material which may become firm and uncomfortable at too low a temperature.

The detector unit 8 detects the temperature before the adjustment starts to provide a starting value to the control unit 4, which determines if cooling or heating is required. Manual control means may also be connected to the control unit to let the user determine if cooling or heating is to be initiated, or both can be initiated at the same time. The detector unit 8 also detects the temperature both during cooling and during heating of the seat 2. During cooling, the detector unit is subject to both conductive and convective cooling, which may result in a measured temperature value representing the cooling, depending on which type of detector unit is used. The control unit 4 may start the electrical heater 3 in connection with the starting of the cooling device 1 or in dependence upon the control algorithm and/or the measured temperature value of the detector unit.

The system according to the first embodiment of the present invention may be supplemented with an additional fan 9 which advantageously may be placed at or in connection with air conditioning equipment 10 already available in the vehicle. The fan 9 of the air conditioning equipment may also replace the fan 6 at the seat 2. The two fans, 6 and 9, may be used separately or in combination. An advantage with such an arrangement is that the fans, 6 and 9, may be used simultaneously in order to increase the amount of air provided to the seat 2. Another advantage is that they may be used separately in order to control the air flow to different locations in the seat 6.

Figure 2:
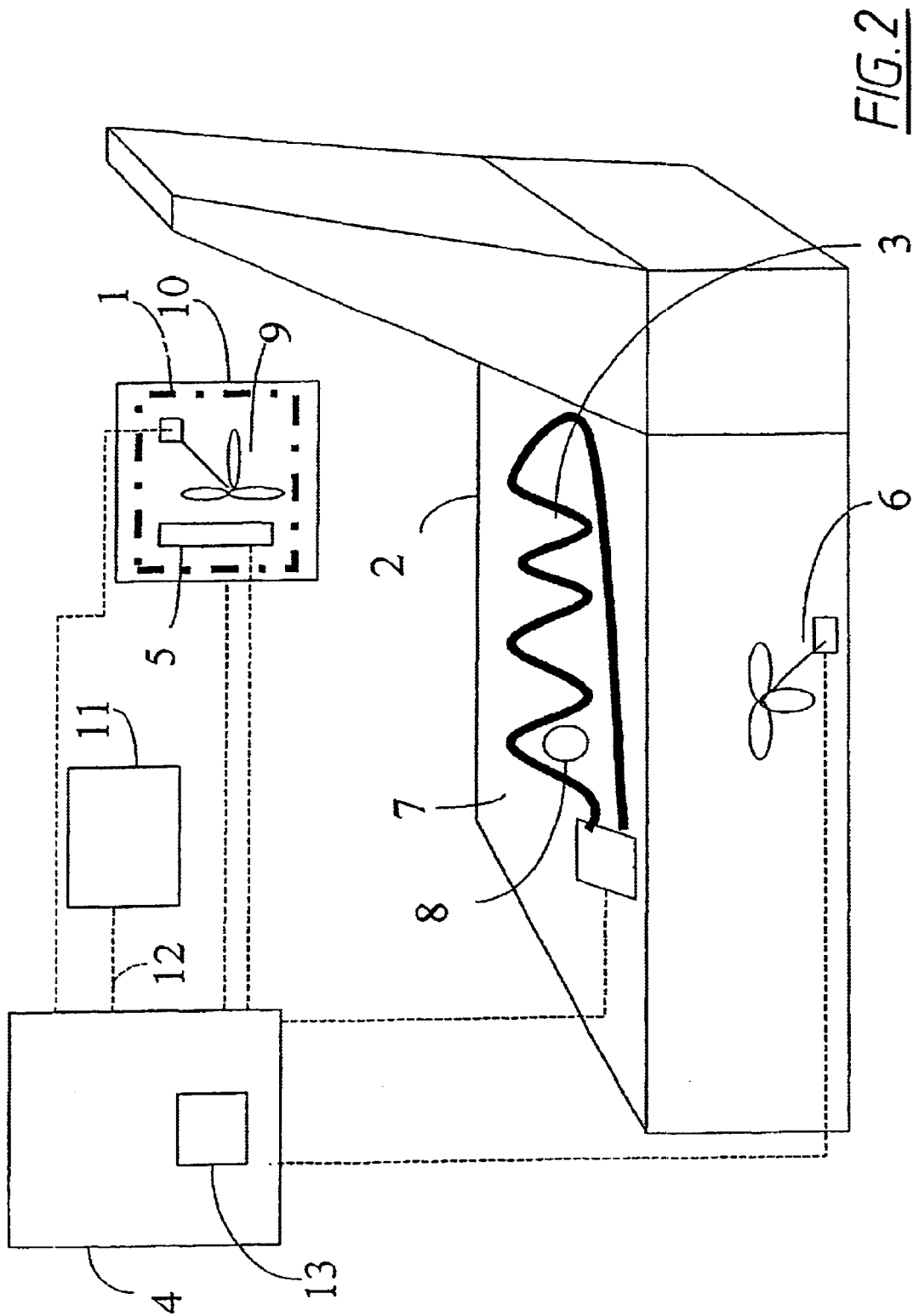
FIG. 2 is a side, elevational, schematic view of a circuit diagram showing a device according to a second embodiment of the present invention.

In FIG. 2, a second embodiment of the present invention is shown, where the detector unit 8 of the electrical heater 3 is used to detect the temperature in the seat 2 and to provide the control unit 4 with information concerning the temperature, where the cooling element 5 is either a separate part connected to the air conditioning equipment 10, or is a part of the air conditioning equipment 10, e.g. "Automatic Climate Control" (ACC), which is normally not placed in the seat 2, but at a suitable place in the car, e.g. the engine housing (not shown). After the cooling element 5, the cooled air is further led from the air conditioning equipment 10 through a conduit (not shown) to the seat 2 where requisite cooling of the seat takes place. The control of the air flow may be executed either by means of a blowing fan 6 placed at or in connection with the air conditioning equipment 10 or in connection with the seat 2. For blowing fans 6 working at a fixed number of revolutions, the air flow may be controlled with suitable choking devices (not shown) which are controlled by the control unit 2. The same advantages that have been mentioned for the first embodiment are acquired in combination with the electrical heater 3.

Figure 3:
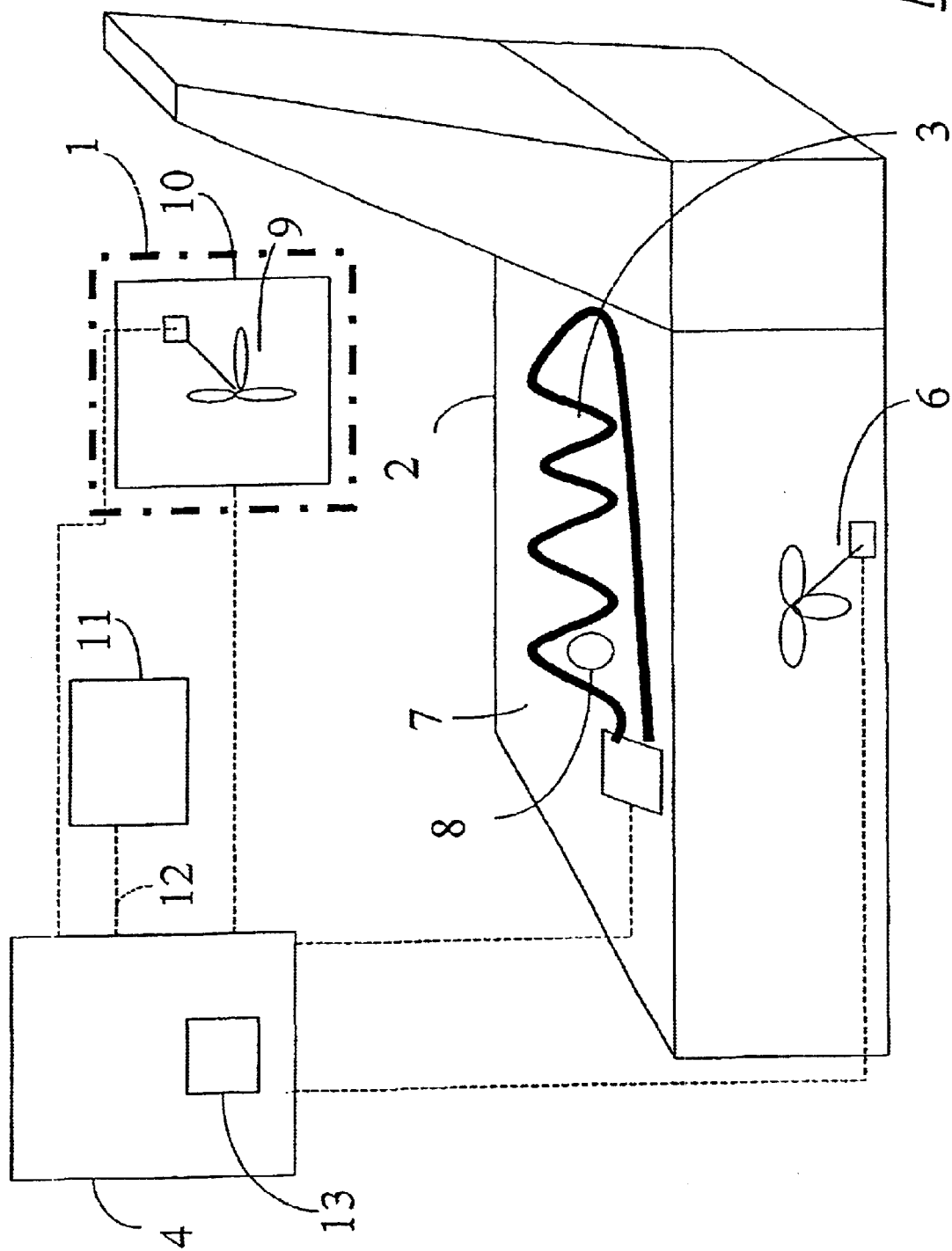
FIG. 3 is a side, elevational, schematic view of a circuit diagram showing a device according to a third embodiment of the present invention.

For a third embodiment, as shown in FIG. 3, where the detector unit 8 of the electrical heater 3 is used to detect the temperature in the seat 2 and to provide the control unit 4 with information concerning the temperature, the air in the passenger compartment that has been cooled by the air conditioning equipment 10 is used for cooling the seat 4. A cooling fan 6 is thus arranged to blow the air in the compartment in such a manner that a partial amount of the air in the compartment may be directed and controlled towards the seat. The blowing fan 6 may be placed in connection with the seat 2, e.g. under the seat 2 or in connection with the air conditioning equipment 10 or in any other suitable place. The same advantages that have been mentioned for the first embodiment are acquired in combination with the electrical heater 3.

Figure 4:
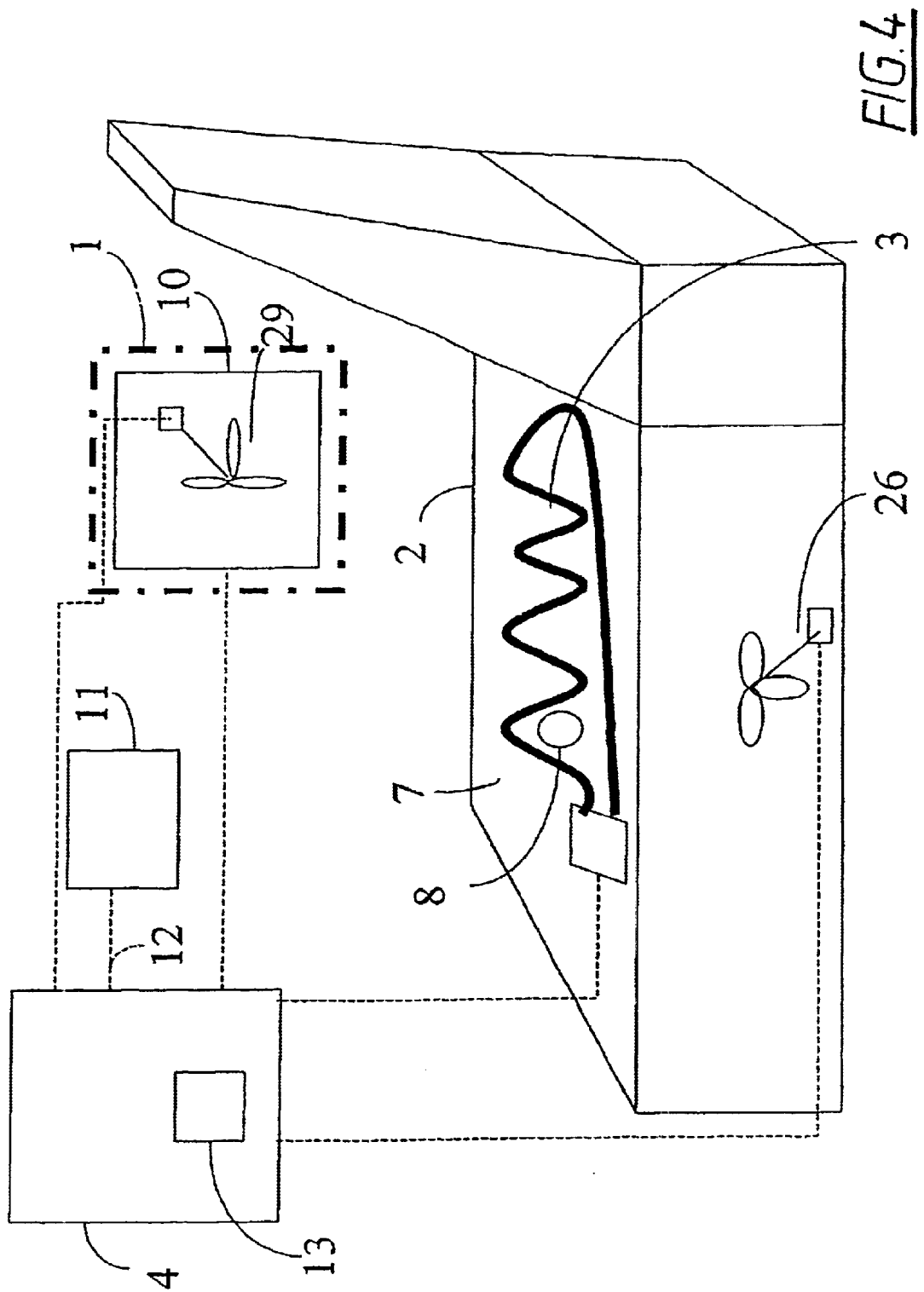
FIG. 4 is a side, elevational, schematic view of a circuit diagram showing a device according to a fourth embodiment of the present invention.

For a fourth embodiment, as shown in FIG. 4, where the detector unit 8 of the electrical heater 3 is used to detect the temperature in the seat 2 and to provide the control unit 4 with information concerning the temperature, the air in the compartment that has been cooled by the air conditioning equipment 10 is used for cooling the seat. A fan, 26, 29, here called induced draft fan, 26, 29, is then arranged to suck the air in the compartment in such a manner that a partial amount of the air in the compartment may be directed and controlled towards the seat and from the surface of the seat towards the floor. The induced draft fan, 26, 29, may be placed in connection to the seat, e.g. under the seat 2, in FIG. 4 marked with reference numeral 26, or in connection with the air conditioning equipment 10, in FIG. 4 marked with reference numeral 29, or in some other suitable place. Alternatively, these two induced draft fans, 26 and 29, may be used in the same arrangement. An advantage that is achieved with the arrangement according to FIG. 4 is that the sensor 8 detects a temperature that, for instance, depends on the air that has just passed the seat surface 7, i.e. the air closest to the user's body, which leads to the control depending on a measured value that is based more on the temperature that corresponds to the target temperature/desired value, i.e. the temperature on the seat surface 7. The same advantages that have been mentioned for the first embodiment are acquired in combination with the electrical heater 3.

Figure 5:
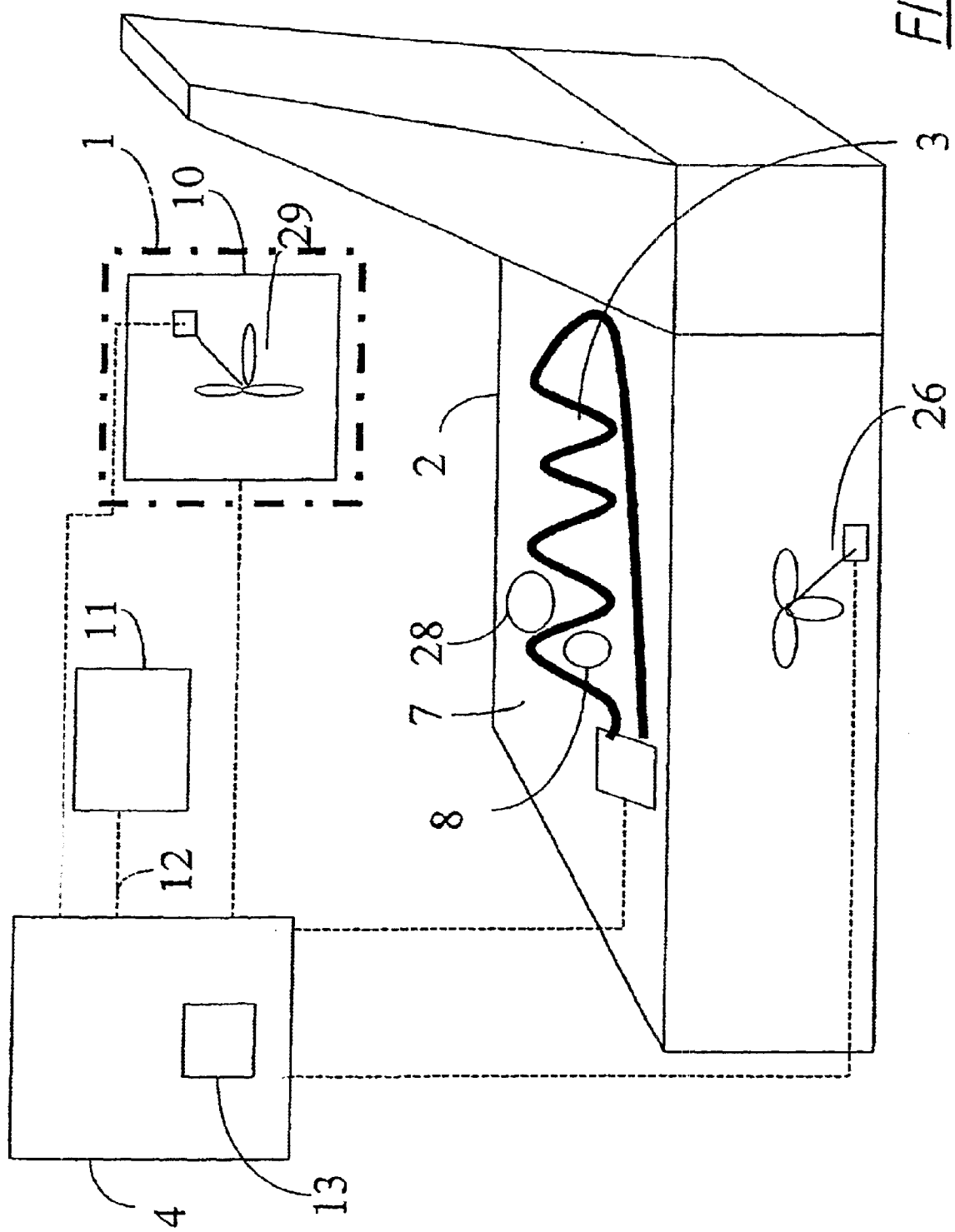
FIG. 5 is a side, elevational, schematic view of a circuit diagram showing a device according to a fifth embodiment of the present invention.

For a fifth embodiment, as shown in FIG. 5, where the detector unit 8 of the electrical heater 3 is used to detect the temperature in the seat 2 and to provide the control unit 4 with information concerning the temperature, the air in the compartment that has been cooled by the air conditioning equipment 10 is used for cooling the seat. The induced draft fan, 26, 29, is then arranged to suck the air in the compartment in such a manner that a partial amount of the air in the compartment may be directed and controlled towards the seat and from the surface of the seat towards the floor. The induced draft fan, 26, 29, may be placed in connection to the seat, e.g. under the seat 2, in FIG. 5 marked with reference numeral 26, or in connection with the air conditioning equipment 10, in FIG. 4 marked with reference numeral 29, or in some other suitable place. In connection with the air flow that has been sucked in after the seat surface 7, downstream the air flow that has just the seat surface 7, i.e. the air closest to the user's body, a humidity sensor 28 is placed, detecting the degree of humidity in the air flow, which degree of humidity thus depends on the user's humidity and the humidity of seat surface 7. The humidity sensor 28 provides information for the control unit 4, which can control the air flow depending on both temperature and humidity. An advantage that is achieved from this arrangement is that an optimal adjustment of the fan 26, the air conditioning equipment 10 and the electrical heater 3 takes place, which optimizes the use of these units and provides for optimum drying and cooling of the user for optimum comfort. The same advantages that have been mentioned for the first embodiment are acquired in combination with the electrical heater 3.

In order to control the apparatus mentioned above, according to all of these embodiments (with reference to FIGS. 1–5), a control unit 4 is used, comprising a communication unit 13 that can communicate with other units, both externally and internally. According to International Application No. PCT/SE99/00261, apparatus and a method are disclosed for heating a vehicle seat, comprising an electrical heater connected to a control unit. The control unit comprises current supply means for supplying a current through the electrical heater allowing it to be heated. There is also a temperature sensor connected to the control unit for detection of the temperature at the electrical heater, where the control unit is arranged for supplying the current if a measured temperature falls below a predetermined desired value. The control unit further comprises a communication unit for reception of information from a separate maneuvering unit by means of a transmission channel for transfer of the information. According to what is disclosed in International Application No. PCT/SE99/00261, at least one function unit for maneuvering the control unit by means of the transferred information is connected to the maneuvering unit. The maneuvering unit thus comprises programmed logic functions for generation of the information, at least dependent upon the condition of the function unit, and programmed functions for sending the information to the communication unit.

The maneuvering unit used in International Application No. PCT/SE99/00261 enables a simplified device and a simplified procedure for heating a vehicle seat. An economically advantageous solution is provided according to what is disclosed in International Application No. PCT/SE99/00261, as the maneuvering unit may be manufactured from proportionately cheap standard electronic components in a very compact fashion, and then programmed to provide necessary functions for, by way of example, the current vehicle model or type of vehicle seat.

The device according to International Application No. PCT/SE99/00261 preferably works completely separately from a central computer unit or the like in a motor vehicle and thus no special adaptations of such a central computer unit is required. The device and the procedure as disclosed in International Application No. PCT/SE99/00261 are based on a modular concept, where great flexibility is acquired with a few uncomplicated electronic components that are possible to standardize.

According to what is disclosed in International Application No. PCT/SE99/00261, the information comprises information concerning the desired temperature, where the maneuvering device is arranged to generate the information starting from information concerning the design of the vehicle seat, stored in the maneuvering device. International Application No. PCT/SE99/00261 thus discloses a device and a procedure that may be used for e.g. control of heat and ventilation according to the present invention.

An arrangement for transfer of information is previously known from International Application No. PCT/SE97/01171. The transfer is controlled by information between the control unit 4 and the central computer unit 11 following a periodic lapse with a certain predetermined period time $t_1$. The information transfer is based on the basic concept that information that corresponds to a certain desired value of the desired temperature value $T_B$ is transferred from the central computer unit 11 to the control unit 4. Preferably, an information transfer also takes place in the opposite direction, i.e. from the control unit 4 to the central computer unit 11. This further piece of information from the control unit 4 may suitably comprise status information. During the complete period $t_1$, a transfer from the control unit 4 to the central computer unit 11 takes place during a certain period of time $t_2$, while the transfer from the central computer unit 11 to the control unit 4 takes place during another period of time $t_3$. The transfer that is disclosed in International Application No. PCT/SE97/01171 may be used in combination with the present invention in such a way that that same equipment may be used at different seats, and only the control algorithm that controls the control procedure has to be changed.

According to International Application No. PCT/SE97/01172 there is a procedure for heating a seat comprising an electrical heater connected to a control unit arranged for supplying current through the electrical heater. According to what is disclosed in International Application No. PCT/SE97/01172, the procedure comprises detection of a current temperature in connection with the electrical heater, and also an adjustment of the temperature by supplying the current through the electrical heater if the current temperature falls below a predetermined desired temperature. According to International Application No. PCT/SE97/01172, the invention is based on the basic concept that it comprises determination of an additional value, $\Delta T$, to the desired temperature $T_B$. This additional value is added to the predetermined desired temperature in connection with such an adjustment. The additional value may be positive or negative. The invention provides for compensation where a slightly "too high" (or "too low") value of the desired temperature is used. Thus, an adjustment with individual adaptation to a certain seat design is supplied, i.e. that the same equipment may be used for different seats, and the only thing that has to be changed is the control algorithm that controls the control procedure, which thus admits use in combination with the present invention.

To sum up, according to known technology, the purpose of the communication unit 13 is principally to see to it that information concerning the desired value $T_B$ for the temperature control of the electrical heater 3 is transferred to the control unit 4 from an external unit in the form of a central computer unit 11. Preferably, the central computer unit 11 is a computer already available in the vehicle that e.g. may be used for the vehicle's climate control equipment, the vehicle's ignition system, or for similar purposes. The transfer of information takes place by means of a transmission channel 12, preferably constituting an electrical wire.

One of the advantages of the present invention is that already available data wires, so-called buses, are used in the car and in the current seat. This reduces the costs for the cooling device that is furnished with the chair, and it saves space. When using a computer as the control unit, great flexibility is achieved for handling changed conditions, i.e. the computer is fed with a suitable algorithm to use for the adjustment. Since the software, i.e. the algorithm, is crucial for the adjustment, the same hardware, fans, electrical heaters, cooling element and sensors may be mounted in seats of different types, which is cost effective. In order to acquire a correct adjustment, it is sufficient if the computer is informed of which kind of seat the hardware has been installed in, after which the computer that is equipped with different parameters for different seats makes adjustments to these conditions. The computer also provides the user with a possibility of changing the comfort by himself as there may be pre-programmed alternatives in the computer which may be chosen by the user, e.g. extra air flow, temperature control depending on the user's clothing, long trip driving or extra fast drying.

Figure 6:
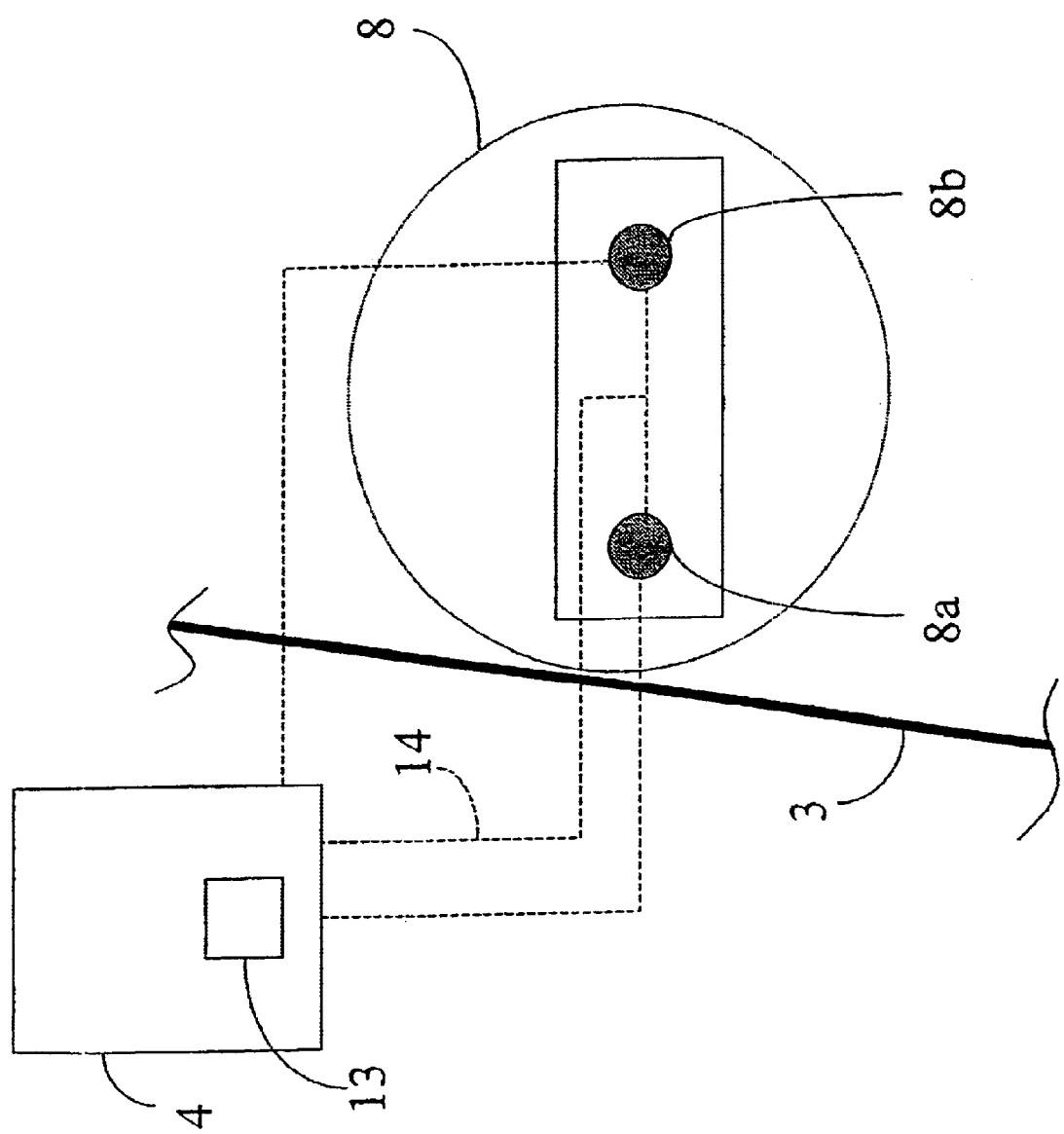
FIG. 6 is a top, elevational, schematic view of a circuit diagram that in an above view shows a detector unit in accordance with known technology, when two temperature sensors in the seat are used during the adjustment.

In connection with the electrical heater 3, the detector unit 8 is arranged, which in turn comprises a first temperature sensor 8*a* and a second temperature sensor 8*b*, which are electrically connected to the control unit 4, as shown in FIG. 6. The temperature sensors preferably consist of thermistors of the NTC (Negative Temperature Coefficient) type, that shows a temperature dependent resistance, $R_1$ and $R_2$, that corresponds to the temperatures, T1 and T2, respectively, that, by placement of the sensors, 8*a* and 8*b*, is detected in connection with the electrical heater 3 and at a predetermined distance from the electrical heater 3, respectively. The first temperature sensor 8*a* may be placed directly on the electrical heater 3 or in the close vicinity of the electrical heater 3. The second temperature sensor 8*b* is placed at a predetermined distance from the electrical heater 3, e.g. between two of the lines defined by the pattern that covers maximum surface in which the electrical heater 3 is laid, or, depending on the seat's design, at another position at a distance from the electrical heater 3, e.g. in the vicinity of the sitting surface.

As the detector unit comprises two temperature sensors, 8*a* and 8*b*, a superposed detected value is acquired, consisting of the sum of the current resistances of the two temperature sensors. This added value then corresponds to a superposed temperature value that during the heating of the seat 2, is compared with a desired value $T_B$, which in turn corresponds to the desired temperature $T_S$, on the surface of the seat. If the detected temperature exceeds the desired value $T_B$, the current supply through the electrical heater will cease, analogous to what has been stated above. The superposed resistance value of the temperature sensors, 8*a* and 8*b*, will consist of two components, partly a first component that is affected by the relatively fast temperature variations of the temperature sensor 8*a* that is placed in the close vicinity of the electrical heater 3, and partly a second component that is affected by the relatively slow temperature variations of the temperature sensor 8*b* that is placed relatively far from the electrical heater 3. Altogether, this provides for a temperature control that corresponds to a balance between a temperature control based on each one of the placements. By a suitable tuning of the placements of the temperature sensors, 8a and 8b, an optimum adapted heating of the seat is obtained, where the desired temperature of the seat's surface is obtained relatively quickly, but without being accompanied by too large temperature variations, which would be the case when a single temperature sensor is placed relatively far from the electrical heater. Neither is the too slow warm-up of the seat obtained, which would be the consequence of a placement of a single temperature sensor placed relatively close to the electrical heater.

Further advantages with a detector unit of this kind are that the first temperature sensor 8a that is placed on or in the vicinity of the electrical heater 3 detects the electrical heater's temperature even during convective cooling of the seat, i.e. with the cooling device 1. The other sensor 8b that is placed at a distance from the electrical heater, on the other hand, senses the convective cooling, which means that convective cooling of the seat 2 affects the other temperature sensor 8b. It is the colder cold of the two temperature sensors, 8a and 8b, that controls the electrical heater's 3 control cycle, which means that the second temperature sensor 8b controls the electrical heater's 3 control cycle during cooling of the seat. A central connection 14 may be placed between the two temperature sensors for diagnostics or as measuring sensors to an algorithm for an enhanced adjustment. When the central connection 14 is used, information about both the temperature and of the electrical heater 3, which is detected by the first temperature sensor 8a, and a temperature at a distance from the electrical heater 3, which is detected by 8b, and that depends on the convective cooling may be provided to the control unit 4.

Further advantages with a detector unit of this kind are that they may be used even when the electrical heater 3 is not turned on, or when an electrical heater is missing to determine temperature differences depending on the user's condition. The first temperature sensor 8a may be placed in the seat on or in the vicinity of the user's body, e.g. under one of the thighs, under the buttocks or behind the back, where the first temperature sensor 8a detects a temperature that depends on the user's temperature and where the air flow is low. The other sensor 8b may be placed where the air flow is higher, i.e. at a distance from the user's body, e.g. between the user's legs. In this case, the central connection 14 may also be used to provide information concerning the two temperature sensors, 8a and 8b, to the control unit, e.g. to determine if one of the temperature sensors detects a temperature that is too cold or too warm in relation to the temperature that the other temperature sensor detects, or if any of the temperature sensors detects a temperature that lies at or over predetermined temperature limits, i.e. too hot or too cold. The information concerning the two temperature sensors provides the control algorithm and thus provides the control unit with the possibility to control e.g. different fans and cooling elements, in order to more precisely control air flow and cooling to local spots in the seat, e.g. to a locally warm spot without lowering the temperature further at an already locally cold spot.

To sum up, it must be mentioned that the present invention uses equipment already available in the seat, such as an electrical heater 3, detector unit 8 and equipment necessary for these units, such as cable pullings, "data buses", control unit 4 and central computer unit 11, which is both economically advantageous and space saving. Further, the method of using electrical heaters 3 for cooling the seat 2 together with a cooling device 1, provides a fast-cooling and fast-drying device with optimum comfort for the user without any convective cooling problems for the user. Further advantages are the increased possibility to more quickly, more accurately and more individually adjust the seat temperature and the dampness of the sitting surface.

Figure 7:
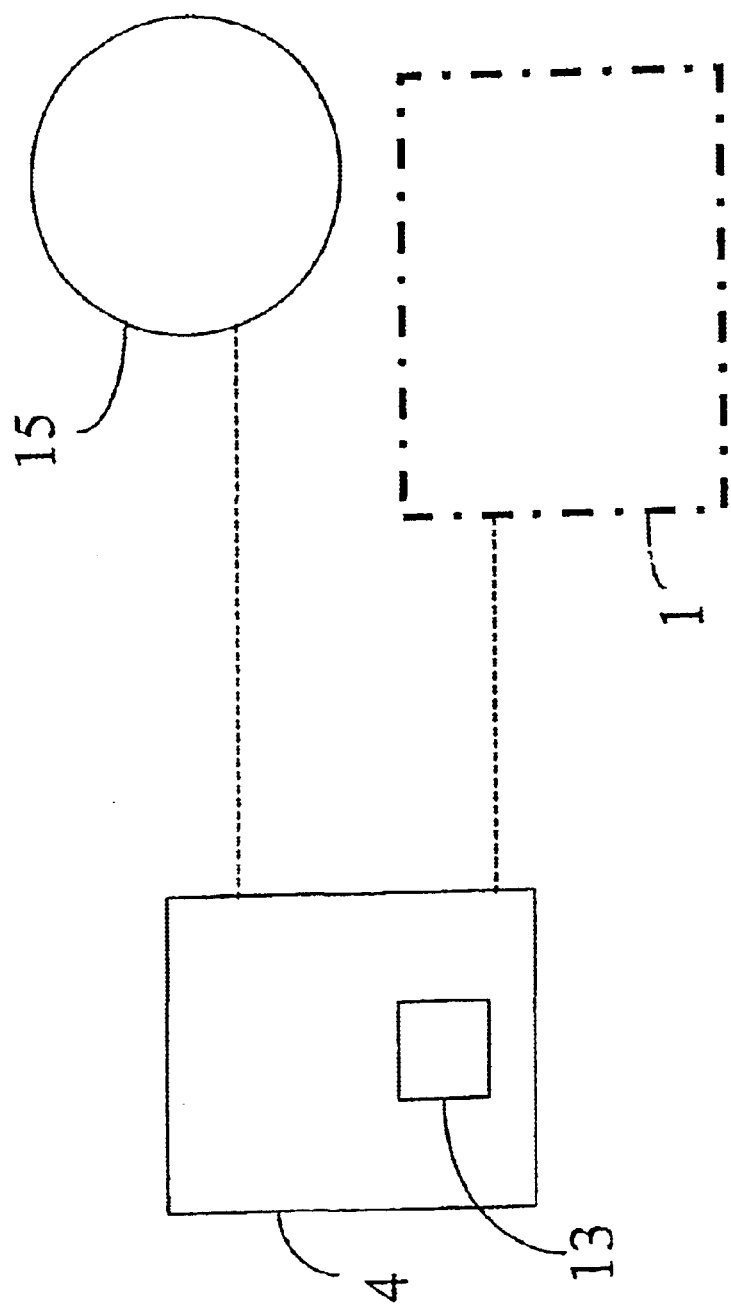
FIG. 7 is a top, elevational, schematic view of a security device according to the present invention.

FIG. 7 shows that the arrangement according to FIGS. 1–6 may also be connected to an external system where an external detector 15 measures the driver's health condition, e.g. by means of an eye detector which measures the eye's activity, a pulse meter, breathing or the like. When the external detector 15 detects that the driver is falling asleep, a signal is provided to the control unit 4 to start an algorithm, such as a health algorithm, where all climate systems available in the vehicle by means of the health algorithm are adjusted to provide a stimulating effect on the driver, e.g. cooling of the seat and thus a cooling of the driver by means of the cooling device 1, or by an increase of the fan velocity and cooling power, or by alternating use of cold, heat and fan, or in any other way that provides a stimulating effect to the driver. The external system may be any system that detects deviations in the behaviour of the driver or the car in relation to a predetermined standard.

Figure 8:
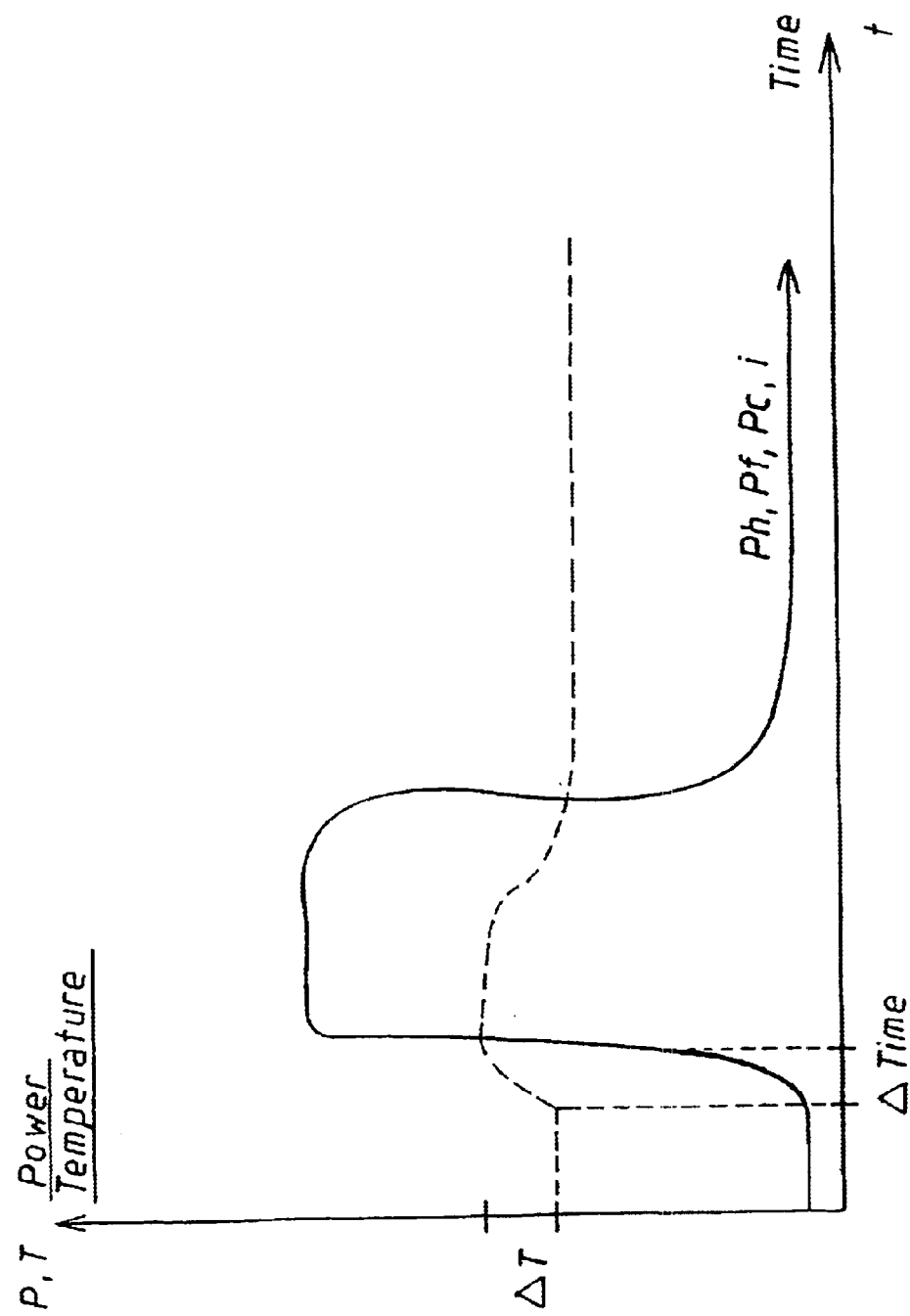
FIG. 8 is a graphical representation of a control algorithm according to the invention.

An algorithm is shown schematically in FIG. 8, i.e. a humidity algorithm, that preferably may be a part of a larger control algorithm for control of a device by means of a control unit described according to any of the embodiments of the invention mentioned above. The humidity algorithm is based on the fact that the material of the seat is known, and on the fact that the humidity content of the air is coupled to the air temperature through the heat capacity of the air, according to known scientific methods, after which a certain predetermined air temperature coupled to a first humidity content of the air and a further air temperature, which air temperature may be measured with e.g. the detector unit 8, coupled to a second humidity content of the air, provides a temperature difference $\Delta T$ and a humidity content difference, which provides a necessary time period $\Delta_{Time}$ calculated in e.g. the central computer unit 11, in order to eliminate the humidity content of the air by ventilation, which consists of the humidity content difference, by the control unit 4 controlling the electrical heater 3 to emit a certain power Ph by current supply, i, and that the fan 6, 9 according to FIGS. 1–3 is controlled to emit a certain flow, a certain power Pf by current supply, i, and possibly also the cooling element 5 is controlled to absorb a certain power Pc by current supply. In FIG. 8, the temperature is shown with a dashed line, and the powers Ph, Pf, Pc and the current intensity with a common solid line, which, however, should not be interpreted to suggest that they supply an equal amount of power or current, but solely as a schematic view of the algorithm as time elapses.

The humidity content and the time period $\Delta_{Time}$ thus may also be acquired as a measured change of the air temperature and the air flow, which provides for control of the electrical heater 3 and/or the fan 6 and/or the cooling element 5.

For certain air flows in combination with a certain temperature change, the air is always dry, i.e. mainly free of humidity, which may be used for control of the electrical heater 3 and/or the fan 6 and/or the cooling element 5 in order to obtain the desired effect, e.g. during drying.

A change in the electrical heater's power in combination with the time t for reaching a certain temperature $T+\Delta T$ starting from a first temperature T, also provides an estimate of the humidity content in the air, which in turn provides the necessary period of time $\Delta_{Time}$ that is used in a humidity control algorithm in the control unit 4 during control of the electrical heater 3 and/or the fan 6 and/or the cooling element 5, and that may be used to provide e.g. a sufficient time period to a timer function at e.g. drying or pre-cooling of the seat.

The present invention is not limited to what has been disclosed above, but different embodiments are possible within the scope of the claims. The fan may for example be controlled by a button maneuvered by the user, or by a chair computer, or by another electronic unit.

The air conditioning equipment 10 described above, may consist of a simple compartment ventilation consisting of a sole fan or by another device appropriate for the purpose.

The present invention may advantageously be used solely for ventilation, i.e. not for cooling, of different seat parts, e.g. the back of a user is often humid and warm why a device or a procedure according to the present invention may be used for the ventilation and/or heating/cooling of the back part of the seat, i.e. for ventilation solely, a fan may be placed in the back part of the seat and for cooling according to the present invention, an electrical heater and a cooling device may be placed in the back part of the seat. According to known technology, an electrical heater and a sensor are often placed in the back part of the seat when it is manufactured.

The cooling device 1 is not tied to what has been mentioned above, but may comprise any kind of cooling element or fan that provides the desired result. The cooling element 1 may e.g. be a part of the air conditioning equipment that is already available, where a cooling agent is led from the air conditioning equipment to a cooling coil (not shown) placed in or in the vicinity of the seat. The fan, 6, 9, 26 and 29, may also be replaced by any kind of blowing/sucking device that provides the desired result. Several fans may be placed in the seat in order to provide a more local influence at certain spots in the seat. There may also be an air distribution system where a multitude of channels leads the air to desired locations in the seat and where the air flow may be determined and conducted by means of special control devices, e.g. flaps, throttling devices etc.

The cooling device may also be used in seats that lack electrical heaters, with a placement of the sensor at a suitable location, e.g. at the seat's surface, for control of the control cycle.

The present invention is also not limited to the usage of a detector unit with two temperature sensors. In principle, conventional NTC or PTC elements with only one sensor may be used.

The temperature sensor and the humidity sensor, respectively, may be of any kind that provides the desired result and may be placed at a suitable place free of choice to provide satisfactory information to the control unit. An advantageous placement of the two sensors should, however, be in the vicinity of the user, i.e. in the vicinity of the seat's surface and/or in the surface of the back part of the seat. The number of sensors is not limited, however, but a number of sensors may advantageously be used, e.g. one sensor for the electrical heater and one for detection of the temperature at a distance from the electrical heater, e.g. in the seat's surface. Aside from different placements of the sensors in the seat, other sensors may also be placed at different locations in the car in order to provide the control unit with information.

The arrangement according to the present invention may also be used for pre-cooling of the seat when the user indicates his presence with e.g. a transmitter, e.g. by unlocking the vehicle and turning the alarm off. The temperature adjustment of the seat then already starts before the user has been seated in the car.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for controlling the temperature of a seat including a lower surface and an upper sitting surface comprising an electrical heater disposed in said seat, cooling means comprising a cooling element and a fan operatively associated with said seat, a detector for detecting the temperature associated with said electrical heater, and a controller for controlling said electrical heater and said cooling means based upon said detected temperature and upon a humidity algorithm comprising a predetermined set of calculations of the humidity of air at a plurality of different temperatures.

2. The apparatus of claim 1 wherein said detector detects said temperature based at least in part upon conductive cooling from said cooling means, convective cooling from said cooling means, and conductive heating from said electrical heater.

3. The apparatus of claim 1 wherein said cooling means is disposed in said seat.

4. The apparatus of claim 1 including an air conditioning unit, and wherein said cooling means is operatively associated with said air conditioning unit.

5. The apparatus of claim 4 wherein said fan is operatively associated with said air conditioning unit.

6. The apparatus of claim 1 wherein said cooling means comprises an air conditioning unit operatively disposed with respect to said seat.

7. The apparatus of claim 6 wherein said fan is operatively associated with said air conditioning unit.

8. The apparatus of claim 1 wherein said fan is disposed to blow air towards said lower surface of said seat and towards said upper sitting surface.

9. The apparatus of claim 1 wherein said fan is disposed to draw air from said upper sitting surface towards said lower surface of said seat.

10. The apparatus of claim 1 including a humidity sensor operatively disposed with respect to said seat for detecting humidity of said upper sitting surface of said seat.

11. The apparatus of claim 1 wherein said detector comprises a first temperature sensor operatively disposed with respect to said electrical heater and at least one second temperature sensor operatively disposed a predetermined distance from said electrical heater.

12. The apparatus of claim 11 wherein said first temperature sensor and said at least one second temperature sensor are connected to each other whereby a superposed detectable temperature value is obtained for said controller.

13. The apparatus of claim 11 including a central connection between said first temperature sensor and said at least one second temperature sensor for providing information with regard to said first temperature sensor and said at least one second temperature sensor to said controller.

14. The apparatus of claim 1 including an auxiliary detector for detecting a standard condition selected from the group consisting of a driver's predetermined standard condition and a vehicle's predetermined standard condition, whereby said auxiliary detector can actuate said cooling means.

15. A method for controlling the temperature of a seat having a lower surface and an upper sitting surface comprising an electrical heater, cooling means, and a detector operatively disposed for detecting a temperature of said electrical heater, and said electrical heater and said cooling means are actuated based upon said detected temperature, said method comprising detecting a first temperature, supplying a predetermined power to said electrical heater, detecting a second temperature at a predetermined time period after said detecting of said first temperature, detecting the temperature difference between said first temperature and said second temperature, determining the humidity content of air from said first and second temperatures and said predetermined power, determining a predetermined time period based upon said humidity content of said air and said first and second temperatures and said predetermined power, and controlling said electrical heater and said cooling means based upon said predetermined time period whereby the humidity content of said air is eliminated.

16. The method of claim 15 including detecting said temperature based upon the conductive cooling from said cooling means, the convective cooling from said cooling means, and the conductive heating from said electrical heater.

17. The method of claim 15 including employing a humidity control algorithm based upon the knowledge that certain air flows in combination with certain temperature changes correspond to air substantially free of humidity, said method including controlling at least one member selected from the group consisting of said electrical heater, said fan and said cooling element during drying of said seat based upon said information fed to said controller.

18. The method of claim 15 comprising detecting a first temperature operatively associated with said electrical heater, detecting a second temperature at a predetermined distance from said electrical heater, whereby said first and second temperatures give rise to a temperature value, and including comparing said temperature value to a desired temperature value for performing said control.

19. The method of claim 18 wherein said first and second temperatures are added to a superposed common temperature value in the interval between said first and second temperatures.

20. The method of claim 15 including detecting a predetermined deviation from a predetermined standard condition selected from the group consisting of a driver's predetermined standard condition and a vehicle's predetermined standard condition, and activating at least said cooling means upon detecting said deviation.

* * * * *